(12) United States Patent
Dorn et al.

(10) Patent No.: US 6,494,716 B1
(45) Date of Patent: Dec. 17, 2002

(54) DENTAL ETCH WITH IMPROVED FLAVOR

(75) Inventors: Alma Dorn, 145 Tanton Hill Rd., Ridgefield, CT (US) 06877; Michelle Verhave, 7 Close Hill Rd., Croton Falls, NY (US) 10519; Joel Ross, Ardsley, NY (US)

(73) Assignees: Alma Dorn, Ridgefield, CT (US); Michelle Verhave, Croton Falls, NY (US)

( * ) Notice: Subject to any disclaimer, the term of this patent is extended or adjusted under 35 U.S.C. 154(b) by 0 days.

(21) Appl. No.: 09/722,974

(22) Filed: Nov. 27, 2000

(51) Int. Cl.[7] .............. A61K 6/00; A61K 7/16; A61K 7/24
(52) U.S. Cl. ............... 433/216; 424/49; 424/55; 424/58; 433/228.1
(58) Field of Search .............. 424/49–58; 433/216, 433/228.1

(56) References Cited

U.S. PATENT DOCUMENTS

| 4,376,673 A | 3/1983 | Cheung .............. 156/662 |
| 5,061,183 A | 10/1991 | Nicholson ........... 433/228.1 |
| 5,256,065 A | 10/1993 | Nicholson ........... 433/228.1 |
| 5,385,728 A | 1/1995 | Suh ................... 424/54 |
| 5,766,012 A | 6/1998 | Rosenbaum et al. ... 433/228.1 |
| 6,342,204 B1 * | 1/2002 | Combe et al. ........ 424/49 |

* cited by examiner

Primary Examiner—Shep K. Rose
(74) Attorney, Agent, or Firm—Kenyon & Kenyon

(57) ABSTRACT

An acid dental etch having improved taste, which comprises an acid in an amount effective to etch a surface of a tooth; a flavoring formulation that improves the flavor of the dental etch and is stable in the acid, in an amount that is effective in improving the flavor of the dental etch; and preferably, sufficient gelling agent to form a gel.

20 Claims, No Drawings

DENTAL ETCH WITH IMPROVED FLAVOR

The present invention relates to the amelioration of the bad taste of dental etching compositions by incorporating a flavor formulation into them that improves their taste.

BACKGROUND OF THE INVENTION

In dentistry, it is sometimes necessary to etch the enamel or dentin surfaces of the teeth with an acid etch, particularly to increase the bonding of a subsequently applied coating to those surfaces. In addition to cleaning those surfaces, the etching also creates micropores and thereby roughens them and increases the mechanical bonding for strength of the coating to be subsequently applied to the roughened surfaces. Generally, the dental etching compositions also contain a gelling agent, the purpose of which is to help the dental etching compositions adhere to the enamel, thereby making the etching composition more effective. Commercially available dental etching gels contain phosphoric acid as the active ingredient. The major problem with currently commercially available dental etching gels, however, is that they have a bad taste. This is particularly a problem where the etches are used on the teeth of children, whose taste buds are particularly acute. Therefore, there is a definite need for a better tasting dental gel that would be more palatable to both young and old alike.

A number of patents mention dental etches, but none of them recognizes the bad taste of the etches, let alone addresses the bad taste and offers a solution to improve the taste. These patents are: U.S. Pat. Nos. 4,376,673; 5,766,012; 5,385,728; 5,256,065 and 5,061,183.

It is understood that one commercially available dental etch comprises water, ethanol, polyglycol, $H_3PO_4$, silica and colorants.

It has now been found that it is possible to improve the taste of dental etching gels by incorporation of a flavoring formulation either into the commercially available dental etching gels or as part of an overall formulation of the dental gel, including the flavoring formulation of the invention.

SUMMARY OF THE INVENTION

It is an object of the present invention to provide a flavoring formulation to improve the bad taste of dental etching gels.

It is an object of the present invention to provide a flavoring formulation that may be incorporated into currently commercially available dental etching gels in order to improve the taste of those dental gels.

It is another object of the present invention to provide a total etching gel that includes the flavoring formulation of the invention in an overall product that has a much better taste than the currently commercially available dental etching gels.

These objects, as well as further objects which will become apparent from the discussion that follows, are achieved, in accordance with the present invention, by an acid dental etch having improved taste, which comprises:
(a) an acid that is effective in etching tooth surfaces in an amount effective to etch a surface of a tooth;
(b) a flavoring formulation that improves the flavor of the dental etch and is stable in the acid, in an amount that is effective in improving the flavor of the dental etch.

The acid is preferably phosphoric acid, which may be present in the etch in an amount of from about 10% to about 40% by weight of the gel. The flavoring formulation comprises a flavoring agent. Examples of flavoring agents are bubble gum flavor, cherry flavor, grape flavor, anise oil, cassia oil, vanilla extract, vanilla creme, orange flavor, anethole, licorice, and spearmint oil. The flavoring formulation may also comprise a sweetener. Examples of suitable sweeteners are neohespiridin dehydrochalcone, xylitol, and Sucralose.

Preferably, the dental etch in one embodiment of the invention also comprises a sufficient amount of gelling agent to form a gel. In the total acid gel of the invention, the gelling agent may be comprised of sodium alginate, a sequestrant, and a source of calcium. Preferably, the sequestrant is sodium citrate. The source of calcium may be dicalcium phosphate. In another embodiment of the invention, the gelling agent may be silica.

PREFERRED EMBODIMENTS OF THE INVENTION

The acid dental etching gel composition having improved taste comprises an acid in an amount effective to etch the enamel or dentin of a tooth; a flavoring formulation that improves the flavor of the dental etching gel composition and is stable in the acid, in an amount that is effective in improving the flavor of the dental etch; and sufficient gelling agent to form a gel.

Preferably, the acid is phosphoric acid. The acid may be present in the etch in an amount of from about 10% to about 40% by weight of the gel composition. Preferably, the acid is present in the etch in an amount of at least about 25% by weight of the gel composition. More preferably, the acid is present in the etch in an amount of from about 30% to about 40% by weight of the gel composition. The usual formulation contains about 35% of the acid by weight of the gel composition.

The flavoring formulation comprises a flavoring agent. Preferably, the flavoring agent is selected from the group consisting of a bubble gum flavor, a cherry flavor, grape flavor, anise oil, cassia oil, vanilla extract, vanilla creme, orange flavor, anethole, licorice, spearmint oil, phenylacetaldehyde diisobutyl acetal, and mixtures thereof. Children prefer bubblegum, grape and strawberry flavors. Adults prefer mint and vanilla flavors. The amount of the flavoring agent is from about 5 percent to about 25 percent.

The flavoring formulation may also comprise a sweetener. Preferably, the sweetener is selected from the group consisting of neohespiridin dehydrochalcone, xylitol, Sucralose, and mixtures thereof. An effective amount of the sweetener is used, e.g., from about 0.5 percent to about 50 percent.

In one embodiment of the invention, the gelling agent may be comprised of sodium alginate, a sequestrant, and a source of calcium. Preferably, the sequestrant is sodium citrate. Preferably, the source of calcium is dicalcium phosphate. An effective amount of sodium alginate is from about 1 percent to about 5 percent. The effective amount of sequestrant is preferably from about 0.5 percent to about 3 percent. The amount of the source of calcium is from about 0.05 percent to about 2 percent.

When a sodium alginate, e.g., Keltone HV, is used, it requires a cross-linking agent, e.g., a calcium salt, and a sequestrant in order to properly gel. However, when an alkylene glycol alginate is used, neither a calcium salt nor a sequestrant is required in order to gel. The alkylene group may contain from 2 to about 6 carbon atoms. The alkylene glycol alginate should be non-toxic. Preferred is from about 1 to about 15 percent of proylene glycol alginate, which is commercially available as Kelcoloid HVF. When using Kelcoloid HVF, it is preferred to hydrate it first and then add the flavoring agent and the acid etching compound. The gelling agent is stable in the low pH environment caused by the acid etching compound.

In another embodiment of the invention, the gelling agent may be comprised of silica in an amount of from about 4% to about 18% of the total formulation. Preferably, the silica is present in an amount of from about 4.5% to about 7% of the total formulation. Most preferably, the silica is present in an amount of about 5%. Generally, the smaller particle sizes are preferred. A minimum of 200 screen size is preferred.

In this embodiment of the invention, water, ethanol, polyglycol and colorants may also be present in the formulation:

Water may be present in an amount of from about 20% to about 45% of the total formulation. Preferably, water is present in an amount of from about 23% to about 34% of the total formulation. Most preferably, water is present in an amount of about 23%.

Ehtanol may be present in an amount of from about 8% to about 14% of the total formulation. Preferably, ethanol is present in an amount of from about 8% to about 11% of the total formulation. Most preferably, ethanol is present in an amount of about 9%.

Polyglycol may be present in an amount of from about 3% to about 5% of the total formulation. Preferably, polyglycol is present in an amount of from about 3% to about 4% of the total formulation. Most preferably, polyglycol is present in an amount of from about 3% to about 3.5% of the total formulation.

Colorant may be present in an amount of from about 0.005% to about 0.15% of the total formulation. Preferably, colorant is present in an amount of from about 0.005% to about 0.01% of the total formulation. Most preferably, colorant is present in an amount of about 0.006%. Illustrative of colorants that may be used are FD&C Blue, titanium dioxide, turmeric yellow, and the like.

The following Examples provide samples of the preferred embodiments of the invention.

EXAMPLE 1

The goal is to improve the flavor and acceptance of a phosphoric acid-containing dental etching gel used to "rough-up" teeth prior to bonding and other dental techniques.

Starting material: two syringes, each containing 2 mls of a commercially available blue colored etching gel containing of 40% $H_3PO_4$ (Henry Schein, Inc., Melville, N.Y.)

The following concentrations of dental etching gels are available and effective: 10% etching gel, 35%, and 40%. These are good guidelines. If 10% acid etch is sold, it must also still work. It may be easiest to start with a 25% gel (which presumably may not taste as intense as the 40% gel) and dilute down with sweeteners and flavors to 10%.

Tested for use as additives to enhance flavors, were, e.g., Magnasweet, and samples of liquid bubble gum and cherry flavors (Quest International, Hoffman Estates, Ill.).

Object

To determine taste acceptability of variously diluted etching gels (35% down to 15%) to which liquid cherry and bubble gum flavors have been added.

Method

Test the pH of gel and pH of liquid flavorings:

Gel pH=1.0

Quest #7Y16969 Bubble gum (BG) Artificial flavor pH=3.5

Quest #DY09152 Cherry (CH) Artificial flavor pH=2.5

Start with 2 syringes, each containing 1.2 ml of 40% gel. Syringe barrel length=38 mm/1.2 ml, therefore 0.4 ml of gel would be contained in 12.66 mm. Mark the barrel at 12.66 mm intervals in order to deliver 0.4 ml gel increments.

TABLE I

| Test tube # | 40% Gel in tube | Amt. of liquid flavor added | Final Phosphoric Acid concentration | Texture/Taste final dilution |
|---|---|---|---|---|
| BG1 | 0.4 ml | +0.0571 ml | 35% | loose gel/extremely sour; no bubble gum taste |
| BG2 | 0.4 ml | +0.24 ml | 25% | too loose/still very sour and no bubble gum taste |
| BG3 | 0.4 ml | +0.666 ml | 15% | much too loose/less sour but not a pleasant taste |
| CH1 | 0.4 ml | +0.0571 ml | 35% | still thick gel/ extreme sour, slight cherry taste |
| CH2 | 0.4 ml | +0.24 ml | 25% | immiscible; poured off upper flavor layer and used gel for the following sweetening expt. |
| CH3 | 0.4 ml | +0.666 ml | 15% | immiscible; poured off upper flavor layer and used gel for the following sweetening expt. |

Conclusions

1) Dilution of the etching gel to 25% or less markedly reduces the gel viscosity and the gel may not be retained on tooth surfaces well enough.

2) A sweetener is needed to mask the sourness. Try xylitol, sorbitol, erythritol and possibly Magnasweet.

Object

To test the effect of adding sweeteners to flavored etching gels.

Method

Into BG1 (total vol.=0.457 ml), add 50 mg xylitol (=109.4 mg xylitol/ml): still very sour.

Into BG2 (total vol.=0.64 ml), add 100 mg sorbitol (=156.25 mg sorbitol/ml): even more sour.

Into CH1 (total vol.=0.457 ml), add 100 mg erythritol (+218.8 mg erythritol/ml): slightly more acceptable but still very sour.

Into CH2 (total vol.=0.457 ml), add 200 mg xylitol (=437 mg xylitol/ml): much too sour.

Into CH3 (total vol.=0.457 ml), add 236 mg erythritol (=516 mg erythritol/ml): didn't dissolve completely; still not acceptable.

Into BG1, add another 250 mg xylitol (=656 mg xylitol/ml): still unacceptable but less bitterly sour.

Into BG2, add 250 mg xylitol (=156.25 mg sorbitol and 390 mg xylitol/ml: very sour.

Into CH1, add 350 mg erythritol (+984 mg erythritol/ml): most acceptable so far.

Into CH2, add 400 mg erythritol (+437 mg xylitol/ml and 875 mg erythritol/ml: better but still not as good as CH1.

Into CH3, add 500 mg xylitol (=516 mg erythritol/ml and 1094.9 mg xylitol/ml): most acceptable, but not pleasant.

Into BG1, add 0.3 ml honey: pretty good. BEST

Into BG2, add 0.3 ml honey: not quite so good

Into CH1, add 0.3 ml honey: slightly better

Into CH2, add 0.3 ml honey: slightly better

Into CH3, add 0.3 ml honey: better

|  |  | % of final solution |
|---|---|---|
| BEST FORMULAS SO FAR: | | |
| BG1: | 0.4 ml 40% Phosphoric acid (15.1% final conc.) | 37.8% |
|  | 0.057 ml bubble gum flavor liquid | 5.39% |
|  | 300 mg xylitol (assume vol. of 0.1 ml) | 28.3% |
|  | 0.3 ml honey | 28.3% |
|  | 1.057 gm | 99.8% |
| and possibly | | |
| CH3: | 0.4 ml 40% Phosphoric acid (10.7% final conc.) | 26.7% |
|  | 0.06 ml cherry flavor liquid | 4.0% |
|  | 236 mg erythritol | 15.7% |
|  | 500 mg xylitol (assume vol. of 0.24 ml) | 33.4% |
|  | 0.3 ml honey | 0.2% |
|  | 1.496 gm | 99.8% |

Object

Test fructose and xylitol as sweeteners along with various flavors to mask 0.3 ml Dentsply (50% buffered Phosphoric acid Tooth conditioner) in test tubes.

TABLE II

| Test tube # | Sweetener added | Flavor(s) added | Comments |
|---|---|---|---|
| 1 | 200 mg fructose | 50 µl anethole | fructose not fully soluble; pretty good taste |
| 2 | 200 mg xylitol | 50 µl anethole | very good, better than |
| 3 | 200 mg xylitol | 50 µl anise oil | similar, also fairly good |
| 4 | 200 mg xylitol/ 50 fructose | 50 µl wintergreen | not good |
| 5 | 250 xylitol | 50 µl spearmint oil | not good |
| 6 | 250 xylitol | 50 µl peppermint oil | not good; added 25 µl cherry: still not good |
| 7 | 300 mg xylitol | 50 µl cassia oil (Polarome D-12541) | pretty good |
| 8 | 300 mg xylitol | 25 mg menthol crystals/ 25 µl ethanol | not good; added 25 µl cherry: still not good |
| 9 | 300 mg xylitol | 50 µl cassia oil/25 mg Dragoco artif. chocolate | bad |
| 10 | 300 mg xylitol | 100 µl Shoprite pure vanilla extract/25 µl anethole | best so far |
| 11 | 300 mg xylitol | 100 µl Shoprite pure vanilla/ 25 µl cassia oil | not as good as #10 |
| 12 | 300 mg xylitol | 100 µl Shoprite pure vanilla/ 25 mg Dragoco orange powder | pretty good |
| 13 | 300 mg xylitol | 100 µl Shoprite pure vanilla/ 25 mg Dragoco orange powder/25 µl anethole | very best, complex flavor |
| 14 | 200 mg fructose | 50 µl anethole/100 µl vanilla creme #2961 | very acceptable |
| 15 | 200 mg xylitol | 50 µl anethole/100 µl vanilla #3043 | slightly more sour than #14 |
| 16 | 200 mg xylitol | 50 µl anise oil/50 µl licorice #5701 | also pretty good |
| 17 | 200 mg xylitol/ | 50 µl wintergreen/ 100 µl vanilla creme | confusing taste, still sour |
| 18 | 250 mg xylitol | 50 µl spearmint oil/ 100 µl licorice #5701 | pretty good |
| 19 | 250 mg xylitol | 50 µl peppermint/25 µl Quest cherry #DY09152/ 100 µl vanilla creme | confusing taste, still sour |
| 20 | 300 mg xylitol | 100 µl Shoprite vanilla/ 25 µl anethole/25 µl licorice | excellent |
| 21 | 300 mg xylitol | 100 µl Shoprite vanilla/ 25 µl cassia oil/25 µl licorice | cinnamon (cassia) flavor predominates too much |

TABLE II-continued

| Test tube # | Sweetener added | Flavor(s) added | Comments |
|---|---|---|---|
| 22 | 300 mg xylitol | 100 μl Shoprite vanilla/ 25 μl anethole/25 mg Dragoco orange/25 μl licorice | interesting taste, good |

(Tasted tubes #14, 16, 18, 20 and 22 five days after formulation to do an early stability test.
All tasted very good considering the starting concentration of 50% phosphoric acid.)

Conclusion

Some combination of vanilla creme, anethole, licorice and possibly orange should mask the Phosphoric acid very well with xylitol/fructose. ****NOW TRY FRUTAROM NHDC (neohesperidin dihydrochalcone) to replace some of or all of the sweeteners.

Object

To test the sweetening effect of NHDC (neohesperidin dehydrochalcone) on 0.3 ml of Dentsply 50% Phosphoric Acid Tooth Conditioner.
  **Note: NHDC is not water soluble, but particles are extremely sweet and very few are needed for significant sweetening. NHDC has a mild licorice taste of its own.

TABLE III

| Test tube # | Sweetener added | Flavor(s) added | Comments |
|---|---|---|---|
| 23 | ~1 mg | | appears cloudy as if colloidally suspended; taste is not bad |
| 23 | added another ~3 mg | | very acceptable |
| 24 | ~5 mg | | excellent!! |
| 25 | | 25 μl Frutarom Artif. Vanilla #913097 | no detectible vanilla taste and slightly sour |
| 25 | added ~5 mg | | excellent taste but precipitate (ppt) formed |
| 26 | ~5 mg | 50 μl Vanilla #913097 | ppt. formed |
| 27 | ~5 mg | 50 μl Mother Murphy's Vanilla creme #2961 | no ppt.; best so far |
| 28 | ~5 mg | 50 μl Mother Murphy's Vanilla #3043 | more insoluble particles visible; slightly less so than #27 |
| 24 ↓ | (already had ~5 mg) | 75 μl Vanilla creme #2961 | even better!! |
| 24 ↓ | (already had ~5 mg) | (already had 75 μl vanilla creme); add 25 μl Mother Murphy's licorice #5701 | Excellent, well balanced flavor! Very best so far |
| 24 | (already had ~5 mg) | add 100 mg xylitol | Even better; sweetest |
| 23 | (already had ~4 mg) | 25 μl spearmint | Initial taste is good but after taste isn't |

So far these appear to be the favorites;
18:
  0.3 ml Dentsply (50% phosphoric acid)
  250 mg xylitol (Roquette xylisorb 300)
  21.4% 50 μl spearmint oil (Frutarom)
  final 100 μl Nat. & Artif. Licorice (Mother Murphy's Lab #5701)
  conc. 0.7 ml
  $H_3PO_4$
20:
  0.3 ml Dentsply
  300 mg xylitol
  20% 100 μl vanilla (Shoprite)
  final 25 μl anethole (Frutarom)
  conc. 25 μl Nat. & Artif. licorice
  $H_3PO_4$ 0.75 ml
22:
  0.3 ml Dentsply
  300 mg xylitol
  19.3% 100 μl vanilla (Shoprite)
  final 25 μl anethole
  conc. 25 mg Nat. Orange (Dragoco 9/798297)
  25 μl Nat. & Art. licorice
  0.775 ml
24:
  0.3 ml Dentsply
  5 mg NHDC (Frutarom #112055, Neohesperidin dihydrochalcone)

30% 75 μl Nat. & Artif. Vanilla Creme flavor (Mother Murphy's #2961)
final 25 μl Nat. & Artif. licorice
conc.
   100 mg xylitol
   0.5 ml Rec'd 250 gm sample of 25% McNeil Labs SUCRALOSE aqueous concentrate. At pH 1.0, Sucralose will lose 52% of its sweetness at 25° C. in 6–12 months. However, at pH 2.0, it will only lose 10% at 6 months and 17% at 1 year. For greater than 6 months stability, the pH must be raised to at least 2.

Keep experimenting with 0.3 ml Dentsply per tube and: 300 mg xylitol, 5 mg NHDC, Sucralose, 25–50 μl anethole, 50 μl anise oil, 50 μl spearmint oil, 25 μl licorice #5701, 50–100 μl vanilla #3043, and 50–100 μl vanilla creme.

EXAMPLE 2

Method

Keltone HV is an alginate gel requiring an acid (in these examples, phosphoric), a sequestrant (sodium citrate) and a calcium source (dicalcium phosphate). Approximate proportions to start with are Keltone HV-15 parts, sodium citrate-8 parts, dicalcium phosphate-1 part.

Tube #47

To sample #31, added 15 mg of Keltone HV: thickened somewhat, but not into a gel. Added 1 mg dical. phos. (DCP): still didn't thicken much more Added another 1 mg DCP: thickened slightly Added another 15 mg Keltone HV: thickened more, but still should be even thicker to be of proper viscosity.

Tuber #48

To sample #34, added 70 mg Keltone HV+5 mg DCP: didn't thicken much at all Added 30 mg sodium citrate: thickened to a pretty good texture and tastes great!

TABLE IV

| Tube # | Sweeteners | | | Flavor(s) added | Comments |
|---|---|---|---|---|---|
| | Xyl. | NHDC | Sucralose | | |
| 29 | 0.3 gm | 5 mg | — | 25 μl spearmint | good, can use more mint |
| 30 | 0.3 gm | 5 mg | — | 50 μl spearmint | excellent |
| 31 | 0.3 gm | 5 mg | — | 75 μl spearmint | still better but bitter under tongue when rinsed |
| 32 | — | — | 25 μl | 25 μl spearmint | better than 31, nicer sweetness |
| 33 | — | — | 25 μl | 50 μl spearmint | Best!, add sweetness |
| 34 | — | — | 50 μl | 50 μl spearmint | Excellent, long lasting sweetness |
| 35 | — | — | 25 μl | 25 μl spearmint + 25 μl anethole | Most pleasant so far; balanced flavor and sweetness |
| 36 | — | — | 25 μl | 25 μl spearmint 25 μl vanilla #3043 | good but can't taste mint |
| 37 | — | — | 25 μl | 50 μl spearmint + 25 μl vanilla #3043 | not sweet enough |
| 38 | — | — | 50 μl | 50 μl spearmint + 25 μl vanilla #3043 | Very good |
| 39 | — | — | 25 μl | 25 μl spearmint + 25 μl vanilla creme #2961 | Add spearmint |
| 40 | — | — | 25 μl | 50 μl spearmint + 25 μl vanilla creme #2961 | Add sucralose |
| 41 | — | — | 50 μl | 50 μl spearmint 25 μl vanilla creme #2961 | Very good, better than #38 |
| 42 | — | — | 25 μl | 25 μl spearmint + 12.5 μl licorice #5701 | Add more spearmint |
| 43 | — | — | 25 μl | 50 μl spearmint + 12.5 licorice #5701 | Add more Sucralose |
| 44 | — | — | 50 μl | 50 μl spearmint + 12.5 μl licorice #5701 | Pretty good |
| 45 | — | — | 25 μl | 25 μl spearmint + 25 μl anethole + 25 μl vanilla creme #2961 | Excellent! Add spearmint and Sucralose |
| 46 | — | — | 38 μl | 38 μl spearmint + 25 μl anethole + 25 μl vanilla creme #2961 | PERFECT! |

TABLE V

| New tube # | Old tube # | Keltone HV added | DCP added | Sod. Citr. added | Comments |
|---|---|---|---|---|---|
| 49 | 35 | 50 mg | 5 mg | 30 mg | thickened but not enough |

TABLE V-continued

| New tube # | Old tube # | Keltone HV added | DCP added | Sod. Citr. added | Comments |
|---|---|---|---|---|---|
| 50 | 38 | 50 mg | 5 mg | 50 mg | may be thick enough |
| 51 | 41 | 70 mg | 5 mg | 30 mg | not thick enough |
| 52 | 44 | 70 mg | 5 mg | 50 mg | not thick enough |
| 53 | 46 | 50 mg | 10 mg | 30 mg | pretty good viscosity |

These 5 tubes (49–53) were evaluated for taste.
In the foregoing experiment, Kelco HV sodium alginate was used. Kelco HV requires a calcium salt and a sequestrant in order to properly gel. For the following experiments, Kelcoloid HVF propylene glycol alginate was used and did not require a calcium salt and a sequestrant to properly gel.

Experiment 1

Object
  Make flavored etching gel using flavor ingredients from samples #50 and #53. Compare gelation using Kelcoloid HVF which is added to the flavored phosphoric acid vs gelation resulting from first hydrating the Kelcoloid and then adding flavors and phosphoric acid to it.

Method
  Experiment first using only formula #38—first add 0.3 ml Dentsply (50% phosphoric acid) into tube #54. Then add 50 ul Sucralose, 50 ul spearmint, 25 ul vanilla #3043. Finally add 15 mg Kelcoloid HVF. Shake.

Results
  Didn't dissolve or thicken at all. Tried adding more water to allow hydration: added 0.6 ml, shake. Never thickened. It appears that the Kelcoloid HVF must be hydrated first.

In a separate tube (A), hydrate the Kelcoloid HVF first:
  into 1 ml water, add 15 mg Kelcoloid powder and shake . . . slight thickening; added additional 15 mg . . . became very viscous and clear. 30 mg Kelcoloid HVF/ml is a good concentration.

Tube #55
  Into tube (A) add 0.3 ml Dentsply, 50 ul Sucralose, 50 ul spearmint, and 25 ul vanilla #3043. Total volume is now:

| | |
|---|---|
| 1.0 ml | hydrated Kelkoloid |
| 0.3 ml | Dentsply |
| .125 ml | Sucralose and flavors |
| 1.425 ml | Therefore original 50% Dentsply (0.3 ml) is diluted 4.75 X = 10.52% phosphoric acid. May be too low for etching. For coloring, added 0.5 mg Hilton Davis FD&C blue No. 1 and Warner Jenkinson white color (0.1 mg titanium dioxide) |

Viscosity of final liquid should be a little thicker.
Stock Hydrated Mixture
  In a beaker with a stirring bar, hydrate Kelcoloid HVF by adding water in the proportion of 30 mg/0.8 ml=600 mg/16 ml. While stirring, it became so viscous that it was suspected that it actually may not be fully hydrated and might need more water for this quantity of gel powder.

Based on flavors in previous sample #38:
Tube #56
  Into tube add 0.3 ml Dentsply (50% phosphoric acid)

| |
|---|
| 50 ul Sucralose |
| 50 ul spearmint |
| 25 ul vanilla #3043 mix thoroughly, then add 0.8 ml hydrated Kelcoloid (=30 mg/l 1.225 ml |
| 1.225 ml total = 24.48 mg/ml therefore original 50% Dentsply is diluted 4.08X = 12.25% phosphoric acid |

Experiment 2

Based on flavor in previous sample tube #46, but substituted anise oil for anethol:

| Tube #57 |
|---|
| 38 ul sucralose |
| 38 ul spearmint oil |
| 25 ul anise oil |
| 25 ul vanilla creme #2961: mixed thoroughly, then added |
| 0.3 ml Dentsply, mixed, then added |
| 0.6 ml hydrated Kelcoloid HVF gel from stock solution (=22.5 mg per 1.026 ml = 11.92 mg/ml) |
| 1.026 ml total therefore original 50% Dentsply is diluted 3.42X = 14.7% phosphoric acid |

Tastes very good!

Experiment 3

Using flavor of previous sample #41:

| Tube #58 |
|---|
| 38 ul Sucralose (used less than 50 ul because final vol. will be smaller) |
| 38 ul spearmint oil |
| 25 ul vanilla creme #2961 |
| 0.3 ml Dentsply |
| 0.5 ml hydrated Kelcoloid (30 mg/0.8 ml = 18.75 mg/0.5 ml |
| 0.901 ml total 18.75 mg/.901 ml = 20.81 mg/ml) therefore original 0.3 ml of 50% Dentsply was diluted 3X = 16.6% phosphoric acid |

*Added slightly more titanium dioxide for a whiter and more opaque final color. The final viscosity for some reason is diminished even though Kelcoloid is only 20.81 vs 21.92 in tube #57.

Experiment 4

Based on original flavors in previous tube #46:

| Tube #59 |
| --- |
| 25 ul Sucralose |
| 25 ul spearmint oil |
| 25 ul anethol |
| 25 ul vanilla creme #2961 |
| 0.3 ml Dentsply |
| 0.45 ml hydrated Kelcoloid HVF (=16.875 mg/0.85 ml = 19.85 mg/ml) |
| 0.85 ml total |
| therefore Dentsply was diluted 2.83X = 17.66% phosphoric acid |

Seems to be the best flavor and texture. Although this tube has the least Kelcoloid per ml, because it was mixed more completely and with higher shear force for a longer time; it's more homogeneous than #58 and actually thicker! The amount of Kelcoloid may still be reducible if proper high shear mixing is used.

TABLE VI

| Test Tube # | Formulation | % of Final Solution |
| --- | --- | --- |
| # 1 | 200 mg Fructose | 36.36% |
|  | 50 µl Anethole | 9.09 |
|  | 0.3 ml Dentsply (50% $H_3PO_4$) | 27.27 $H_3PO_4$ |
|  | 0.55 ml |  |
| # 2 | 200 mg Xylitol | 36.36 |
|  | 50 µl Anethole | 9.09 |
|  | 0.3 ml Dentsply | 27.27 $H_3PO_4$ |
|  | 0.55 ml |  |
| # 3 | 200 mg Xylitol | 36.36 |
|  | 50 µl Anise Oil | 9.09 |
|  | 0.3 ml Dentsply | 27.27 $H_3PO_4$ |
|  | 0.55 ml |  |
| # 4 | 200 mg Xylitol | 30.00 |
|  | 50 mg Fructose | 8.33 |
|  | 50 µl Wintergreen Oil | 8.33 |
|  | 0.3 ml Dentsply | 25.00 $H_3PO_4$ |
|  | 0.6 ml |  |
| # 5 | 250 mg Xylitol | 41.67 |
|  | 50 µl Spearmint Oil | 8.33 |
|  | 0.3 Dentsply | 25.00 $H_3PO_4$ |
|  | 0.6 ml |  |
| # 6 | 250 µl Xylitol | 41.67 |
|  | 50 µl Peppermint Oil | 8.33 |
|  | 0.3 ml Dentsply (=50% $H_3PO_4$) | 25.00 $H_3PO_4$ |
|  | 0.6 ml |  |
| # 7 | 300 mg Xylitol | 46.15 |
|  | 50 µl Cassia Oil | 7.69 |
|  | 0.3 ml Dentsply | 23.08 $H_3PO_4$ |
|  | 0.65 ml |  |
| # 8 | 300 mg Xylitol | 44.44 |
|  | 25 mg Menthol Crystals | 3.70 |
|  | 25 µl Ethanol | 3.70 |
|  | 25 mg Cherry | 3.70 |
|  | 0.3 ml Dentsply | 22.22 $H_3PO_4$ |
|  | 0.675 ml |  |
| # 9 | 300 mg Xylitol | 44.44 |
|  | 50 µl Cassia Oil | 7.41 |
|  | 25 mg Artif. Chocolate | 3.70 |
|  | 0.3 ml Dentsply | 22.22 $H_3PO_4$ |
|  | 0.675 ml |  |
| # 10 | 300 mg Xylitol | 41.15 |
|  | 100 µl Vanilla | 13.79 |
|  | 25 µl Anethol | 3.35 |
|  | 0.3 ml Dentsply | 20.69 $H_3PO_4$ |
|  | 0.725 ml |  |
| # 11 | 300 mg Xylitol | 41.38 |
|  | 100 mg Vanilla | 13.79 |
|  | 25 µl Cassia Oil | 3.45 |
|  | 0.3 ml Dentsply (50% $H_3PO_4$) | 20.69 $H_3PO_4$ |
|  | 0.725 ml |  |

TABLE VI-continued

| Test Tube # | Formulation | % of Final Solution |
| --- | --- | --- |
| # 12 | 300 mg Xylitol | 41.38 |
|  | 100 µl Vanilla | 13.79 |
|  | 25 mg Orange | 3.45 |
|  | 0.3 ml Dentsply | 20.69 $H_3PO_4$ |
|  | 0.725 ml |  |
| # 13 | 300 mg Xylitol | 40.00 |
|  | 100 µl Vanilla | 13.33 |
|  | 25 mg Orange | 3.33 |
|  | 25 µl Anethole | 3.33 |
|  | 0.3 ml Dentsply | 20.00 $H_3PO_4$ |
|  | 0.75 ml |  |
| # 14 | 200 mg Fructose | 30.77 |
|  | 50 µl Anethole | 7.69 |
|  | 100 µl Vanilla Creme | 15.38 |
|  | 0.3 ml Dentsply | 23.08 $H_3PO_4$ |
|  | 0.65 ml |  |
| # 15 | 200 mg Xylitol | 26.67 |
|  | 50 µl Anethole | 6.67 |
|  | 100 µl Vanilla | 13.33 |
|  | 0.3 Dentsply (50% $H_3PO_4$) | 20.00 $H_3PO_4$ |
|  | 0.75 ml |  |
| # 16 | 200 mg Xylitol | 30.00 |
|  | 50 µl Anise Oil | 8.33 |
|  | 50 µl Licorice | 8.33 |
|  | 0.3 ml Dentsply | 25.00 $H_3PO_4$ |
|  | 0.6 ml |  |
| # 17 | 200 mg Xylitol | 28.57 |
|  | 50 mg Fructose | 7.14 |
|  | 50 µl Wintergreen | 7.14 |
|  | 100 µl Vanilla Creme | 14.29 |
|  | 0.3 ml Dentsply | 21.43 $H_3PO_4$ |
|  | 0.7 ml |  |
| # 18 | 250 mg Xylitol | 35.71 |
|  | 50 µl Spearmint Oil | 7.14 |
|  | 100 µl Licorice | 14.29 |
|  | 0.3 ml Dentsply | 21.43 $H_3PO_4$ |
|  | 0.7 ml |  |
| # 19 | 250 mg Xylitol | 35.71 |
|  | 25 µl Peppermint | 3.57 |
|  | 25 µl Cherry | 3.57 |
|  | 100 µl Vanilla Creme | 14.29 |
|  | 0.3 ml Dentsply (50% $H_3PO_4$) | 21.43 $H_3PO_4$ |
|  | 0.7 ml |  |
| # 20 | 300 mg Xylitol | 40.00 |
|  | 100 µl Vanilla | 13.33 |
|  | 25 µl Anethole | 3.33 |
|  | 25 µl Licorice | 3.33 |
|  | 0.3 ml Dentsply | 20.00 $H_3PO_4$ |
|  | 0.75 ml |  |
| # 21 | 300 mg Xylitol | 40.00 |
|  | 100 µl Vanilla | 13.33 |
|  | 25 µl Cassia Oil | 3.33 |
|  | 25 µl Licorice | 3.33 |
|  | 0.3 ml Dentsply | 20.00 $H_3PO_4$ |
|  | 0.75 ml |  |
| # 22 | 300 mg Xylitol | 38.71 |
|  | 100 µl Vanilla | 12.90 |
|  | 25 µl Anethole | 3.23 |
|  | 25 mg Orange | 3.23 |
|  | 25 µl Licorice | 3.23 |
|  | 0.3 ml Dentsply (50% $H_3PO_4$) | 19.35 $H_3PO_4$ |
|  | 0.775 ml |  |
| # 23 a | 4 mg NHDC | 1.32 |
|  | 0.3 ml Dentsply | 49.34 $H_3PO_4$ |
|  | 0.304 ml |  |
| # 24 a | 5 mg NHDC | 1.64 |
|  | 0.3 ml Dentsply | 49.18 $H_3PO_4$ |
|  | 0.305 ml |  |
| # 25 | 5 mg NHDC | 1.51 |
|  | 25 µl Vanilla | 7.58 |
|  | 0.3 ml Dentsply | 45.45 $H_3PO_4$ |
|  | 0.33 ml |  |
| # 26 | 5 mg NHDC | 1.41 |
|  | 50 µl Vanilla | 14.08 |
|  | 0.3 ml Dentsply | 42.25 |
|  | 0.355 ml |  |

TABLE VI-continued

| | | |
|---|---|---|
| # 27 | 5 mg NHDC | 1.41 |
| | 50 µl Vanilla Creme | 14.08 |
| | 0.3 ml Dentsply (50% $H_3PO_4$) | 42.25 $H_3PO_4$ |
| | 0.355 ml | |
| # 28 | 5 mg NHDC | 1.41 |
| | 50 µl Vanilla | 14.08 |
| | 0.3 ml Dentsply | 42.25 $H_3PO_4$ |
| | 0.355 ml | |
| #24 b | 5 mg NHDC | 1.32 |
| | 75 µl Vanilla Creme | 19.74 |
| | 0.3 ml Dentsply | 39.47 $H_3PO_4$ |
| | 0.38 ml | |
| #24 c | 5 mg NHDC | 1.23 |
| | 75 µl Vanilla Creme | 18.52 |
| | 25 µl Licorice | 6.17 |
| | 0.3 ml Dentsply | 37.04 $H_3PO_4$ |
| | 0.405 ml | |
| #24 d | 5 mg NHDC | 0.99 |
| | 75 mg Vanilla Creme | 14.85 |
| | 25 mg Licorice | 4.95 |
| | 100 mg Xylitol | 19.80 |
| | 0.3 ml Dentsply | 29.70 $H_3PO_4$ |
| | 0.505 ml | |
| #23 b | 4 mg NHDC | 1.22 |
| | 25 µl Spearmint | 7.60 |
| | 0.3 ml Dentsply (50% $H_3PO_4$) | 45.59 $H_3PO_4$ |
| | 0.329 ml | |
| # 29 | 5 mg NHDC | 0.79 |
| | 300 mg Xylitol | 47.62 |
| | 25 µl Spearmint | 3.97 |
| | 0.3 ml Dentsply | 23.81 $H_3PO_4$ |
| | 0.63 ml | |
| # 30 | 5 mg NHDC | 0.76 |
| | 300 mg Xylitol | 45.80 |
| | 50 µl Spearmint | 7.63 |
| | 0.3 ml Dentsply | 22.90 $H_3PO_4$ |
| | 0.655 ml | |
| # 31 | 5 mg NHDC | 0.74 |
| | 300 mg Xylitol | 44.12 |
| | 75 µl Spearmint | 11.03 |
| | 0.3 ml Dentsply | 22.06 $H_3PO_4$ |
| | 0.68 ml | |
| # 32 | 25 µl Sucralose (25% solution) | 1.79 Sucralose |
| | 25 µl Spearmint | 7.14 |
| | 0.3 ml Dentsply | 42.86 $H_3PO_4$ |
| | 0.35 ml | |
| # 33 | 25 µl Sucralose | 1.67 |
| | 50 µl Spearmint | 13.33 |
| | 0.3 ml Dentsply | 40.00 $H_3PO_4$ |
| | 0.375 ml | |
| # 34 | 50 µl Sucralose | 3.13 |
| | 50 µl Spearmint | 12.5 |
| | 0.3 ml Dentsply | 37.5 $H_3PO_4$ |
| | 0.4 ml | |
| # 35 | 25 µl Sucralose | 1.67 |
| | 25 µl Spearmint | 6.67 |
| | 25 µl Anethole | 6.67 |
| | 0.3 ml Dentsply | 40.00 $H_3PO_4$ |
| | 0.375 ml | |
| # 36 | 25 µl Sucralose | 1.67 |
| | 25 µl Spearmint | 6.67 |
| | 25 µl Vanilla | 6.67 |
| | 0.3 ml Dentsply | 40.00 $H_3PO_4$ |
| | 0.375 ml | |
| # 37 | 25 µl Sucralose (25% solution) | 1.56 Sucralose |
| | 50 µl Spearmint | 12.5 |
| | 25 µl Vanilla | 6.25 |
| | 0.3 ml Dentsply | 37.50 $H_3PO_4$ |
| | 0.4 ml | |
| # 38 | 50 µl Sucralose | 2.94 |
| | 50 µl Spearmint | 11.76 |
| | 25 µl Vanilla | 5.88 |
| | 0.3 ml Dentsply | 35.29 $H_3PO_4$ |
| | 0.425 ml | |
| # 39 | 25 µl Sucralose | 1.67 |
| | 25 µl Spearmint | 6.67 |
| | 25 µl Vanilla Creme | 6.67 |
| | 0.3 ml Dentsply | 40.00 $H_3PO_4$ |
| | 0.375 | |
| # 40 | 25 µl Sucralose | 1.58 |
| | 50 µl Spearmint | 12.5 |
| | 25 µl Vanilla Creme | 6.25 |
| | 0.3 ml Dentsply | 37.50 |
| | 0.4 ml | |
| # 41 | 50 µl Sucralose (25% solution) | 2.94 Sucralose |
| | 50 µl Spearmint | 11.76 |
| | 25 µl Vanilla Creme | 5.88 |
| | 0.3 ml Dentsply (50% $H_3PO_4$) | 35.29 $H_3PO_4$ |
| | 0.425 ml | |
| # 42 | 25 µl Sucralose | 1.72 |
| | 25 µl Spearmint | 6.90 |
| | 12.5 µl Licorice | 3.45 |
| | 0.3 ml Dentsply | 41.38 $H_3PO_4$ |
| | 0.3625 ml | |
| # 43 | 25 µl Sucralose | 1.61 |
| | 50 µl Spearmint | 12.90 |
| | 12.5 µl Licorice | 3.23 |
| | 0.3 ml Dentsply | 38.71 $H_3PO_4$ |
| | 0.3875 ml | |
| # 44 | 50 µl Sucralose | 3.03 |
| | 50 µl Spearmint | 12.12 |
| | 12.5 µl Licorice | 3.03 |
| | 0.3 ml Dentsply | 36.36 $H_3PO_4$ |
| | 0.4125 ml | |
| # 45 | 25 µl Sucralose (25% solution) | 1.56 Sucralose |
| | 25 µl Spearmint | 6.25 |
| | 25 µl Anethole | 6.25 |
| | 25 µl Vanilla Creme | 6.25 |
| | 0.3 ml Dentsply (50% $H_3PO_4$) | 37.50 $H_3PO_4$ |
| | 0.4 ml | |
| # 46 | 38 µl Sucralose | 2.23 |
| | 38 µl Spearmint | 8.92 |
| | 25 µl Anethole | 5.87 |
| | 25 µl Vanilla Creme | 5.87 |
| | 0.3 ml Dentsply | 38.73 $H_3PO_4$ |
| | 0.426 ml | |
| # 47 | 5 mg NHDC | 0.70 |
| | 300 mg Xylitol | 42.13 |
| | 75 µl Spearmint | 10.53 |
| | 0.3 ml Dentsply (50% $H_3PO_4$) | 21.06 $H_3PO_4$ |
| | 2 mg Dicalcium Phosphate | 0.28 |
| | 30 mg Keltone HV | 4.21 |
| | 0.712 ml | |
| # 48 | 50 µl Sucralose (25% solution) | 2.48 |
| | 50 µl Spearmint | 9.90 |
| | 0.3 ml Dentsply (50% $H_3PO_4$) | 29.70 $H_3PO_4$ |
| | 70 mg Keltone HV | 13.86 |
| | 5 mg Dicalcium Phosphate | 0.99 |
| | 30 mg Sodium Citrate | 5.94 |
| | 0.505 ml | |
| # 49 | 25 µl Sucralose | 1.36 |
| | 25 µl Spearmint | 5.43 |
| | 25 µl Anethole | 5.43 |
| | 0.3 ml Dentsply | 32.61 $H_3PO_4$ |
| | 50 mg Keltone HV | 10.87 |
| | 5 mg Dicalcium Phosphate | 1.09 |
| | 30 mg Sodium Citrate | 6.52 |
| | 0.46 ml | |
| # 50 | 50 µl Sucralose | 2.35 |
| | 50 µl Spearmint | 9.43 |
| | 25 µl Vanilla | 4.72 |
| | 0.3 ml Dentsply | 28.30 $H_3PO_4$ |
| | 50 mg Keltone HV | 9.43 |
| | 5 mg Dicalcium Phosphate | 0.94 |
| | 50 mg Sodium Citrate | 9.43 |
| | 0.53 ml | |
| # 51 | 50 µl Sucralose (25% solution) | 2.35 |
| | 50 µl Spearmint | 9.43 |
| | 25 µl Vanilla Creme | 4.72 |
| | 0.3 ml Dentsply (50% $H_3PO_4$) | 28.30 $H_3PO_4$ |
| | 70 mg Keltone HV | 13.21 |
| | 5 mg Dicalcium Phosphate | 0.94 |
| | 30 mg Sodium Citrate | 5.66 |
| | 0.53 ml | |
| # 52 | 50 µl Sucralose | 2.33 |
| | 50 µl Spearmint | 9.30 |
| | 12.5 µl Licorice | 2.33 |
| | 0.3 ml Dentsply | 27.91 $H_3PO_4$ |

TABLE VI-continued

|  |  |  |
|---|---|---|
|  | 70 mg Keltone HV | 13.02 |
|  | 5 mg Dicalcium Phosphate | 0.93 |
|  | 50 mg Sodium Citrate | 9.30 |
|  | 0.5375 ml |  |
| # 53 | 38 μl Sucralose | 1.84 |
|  | 38 μl Spearmint | 7.36 |
|  | 25 μl Anethole | 4.84 |
|  | 25 μl Vanilla Creme | 4.84 |
|  | 0.3 ml Dentsply | 29.07 $H_3PO_4$ |
|  | 50 mg Keltone HV | 9.69 |
|  | 10 mg Dicalcium Phosphate | 1.94 |
|  | 30 mg Sodium Citrate | 5.81 |
|  | 0.516 ml |  |
| # 54 | 50 μl Sucralose (25% solution) | 2.84 |
|  | 50 μl Spearmint | 11.36 |
|  | 25 μl Vanilla | 5.68 |
|  | 15 mg Kelcoloid HVF | 3.41 |
|  | 0.3 ml Dentsply (50% $H_3PO_4$) | 34.09 $H_3PO_4$ |
|  | 0.44 ml |  |
| # 55 | 50 μl Sucralose | 0.87 |
|  | 50 μl Spearmint | 3.51 |
|  | 25 μl Vanilla | 1.75 |
|  | 30 mg hydrated Kelcoloid HVF/ml | 2.10 |
|  | 0.5 mg FD&C Blue No. 1 | 0.035 |
|  | 0.1 mg Titanium Dioxide | 0.007 |
|  | 0.3 ml Dentsply (50% $H_3PO_4$) | 10.52 $H_3PO_4$ |
|  | 1.4256 ml |  |
| # 56 | 50 μl Sucralose | 1.02 |
|  | 50 μl Spearmint | 4.08 |
|  | 25 μl Vanilla | 2.04 |
|  | 30 mg hydrated Kelcoloid HVF/0.8 ml | 2.45 |
|  | 0.5 mg FD&C Blue No. 1 | 0.04 |
|  | 0.1 mg Titanium Dioxide | 0.008 |
|  | 0.3 ml Dentsply (50% $H_3PO_4$) | 12.23 $H_3PO_4$ |
|  | 1.2256 ml |  |

PERCENT FINAL CONCENTRATION IN GEL

| ETCHING GEL COMPONENT | sample numbers | | | |
|---|---|---|---|---|
|  | #56 | #57 | #58 | #59 |
| phosphoric acid | 12.24% | 14.62% | 16.65% | 17.65% |
| spearmint oil (Frutarom) | 4.08% | 3.7% | 4.22% | 2.94% |
| vanilla creme (Mother Mur.) | — | 2.43% | 2.77% | 2.94% |
| vanilla #3043 (Mother Mur.) | 2.04% | — | — | — |
| anethol (Frutarom) | — | — | — | 2.94% |
| anise oil (Frutarom) | — | 2.43% | — | — |
| Kelcoloid HVF | 2.44% | 2.19% | 2.08% | 1.98% |
| Sucralose (McNeil Labs) | 1.02% | 0.93% | 1.05% | 0.74% |
| potassium sorbate | 0.004% | 0.0037% | 0.0042% | 0.0029% |
| sodium benzoate | 0.004% | 0.0037% | 0.0042% | 0.0029% |

EXAMPLE 3

Object

Remake gel sample #59 and try to hydrate the gel with all flavors and sweetener added in first. Then, during hydration, add in phosphoric acid. Try to reduce the amount of Kelcoloid HVF used.

Method

Into test tube #60 (12 mm plastic) add:
  25 ul Sucralose
  25 ul spearmint oil
  25 ul anethole
  25 ul vanilla creme #2961
  0.45 ml water
  approx. 0.5 mg FD&C blue
  approx. 0.1 mg titanium dioxide (white); mix well
Slowly add 15 mg Kelcoloid HVF powder while vortexing.
Finally add 0.3 ml Dentsply (phosphoric acid)

Results

As phosphoric acid was added, mixture became very "clumpy" and was difficult to homogenize.

Conclusion

It's very difficult to properly hydrate a tiny volume of flavored water with the Kelcoloid. Therefore try again to prehydrate the Kelcoloid in a larger vol. of water and use less this time. (<30 mg/0.8 ml). Try 20 mg/0.8 ml=11.25 mg/0.45 ml $$\frac{20 \text{ mg Kelcoloid}}{0.8 \text{ ml}} = \frac{x}{10 \text{ ml}} \qquad x = 250 \text{ mg Kelcoloid}$$

Make stock pre-hydrated gel: Into bottle with 10 ml water, slowly add 250 mg Kelcoloid HVF with constant fast stirring. Extremely thick, so started adding more water: +3 ml, +1 ml. Now stock pre-hydrated gel solution is 250 mg/10 ml+4 ml=14 ml=17.85 mg/ml. Added 16.8 mg Kelcoloid HVF last time in #59 New stock is 17.85 mg/ml=x/0.5 ml x=8.92 mg/0.5 ml Trial #61

25 ul Sucralose
  25 ul spearmint oil
  25 ul anethole
  25 ul vanilla creme #2961
  approx. 0.5 mg FD&C blue
  approx. 0.1 mg titanium dioxide
  0.5 ml new stock sol (contains 8.92 mg/900 ul final vol.=0.99% final concentration mix, then add 0.3 ml Dentsply (50% $H_3PO_4$)
  New total volume is 0.9 ml therefore phosphoric acid is now 50%/3=17.3%
  Final solution is not viscous enough.

Start using 200 μl micropet capillary tubes for higher accuracy on volume measurements:
  200 ul=127 mm in total length
  25 ul=15.875 mm
  50 ul=31.75 mm
  100 ul=63.5 mm Trial #62

Re-do #61 using accurate micropette to test flavors and use of hydrated gel 2 hours later may have allowed for more complete hydration yielding a more viscous gel. Also, add Dentsply to flavors and sweetener first, then add gel.
  25 ul Sucralose
  25 ul spearmint oil
  25 ul anethole
  25 ul vanilla creme #2961
  approx. 0.5 mg FD&C blue
  approx. 0.1 mg titanium dioxide
  0.3 ml Dentsply, mix well then add
  0.5 ml new stock of pre-hydrated gel (contains 8.92 mg Kelcoloid HVF in 900 ul final vol.=0.99% final concentration)
    **During mixing, an immiscible, sticky white precipitate appeared and stuck to the walls of the plastic tube. Could not homogenize. Flavor is very good, so with accurately measured volumes, taste is still good. Try adding phosphoric acid at the end again exactly as in trial #61.

Trial #63
   approx. 0.5 mg FD&C blue
   approx. 0.1 mg titanium dioxide
   25 ul Sucralose
   25 ul spearmint oil
   25 ul anethole
   25 ul vanilla creme #2961
   0.5 ml pre-hydrated gel; mix, then add 0.3 ml Dentsply.
      **Added too much color and couldn't see clearly the texture and degree of homogenization after mixing. Did see precipitate on the test tube walls. Try adding Dentsply first.
Trial #64:
   0.3 ml Dentsply
   approx. 0.5 mg FD&C blue→became yellow, not blue
   approx. 0.1 mg titanium dioxide
   25 ul sucralose→turned green
   25 ul spearmint oil
   25 ul anethole→turned darker green
   25 ul vanilla creme #2961
   0.5 ml pre-hydrated gel→as the gel went into the bottom of the tube, color became darker green. Ultimately became too dark green. Still seeing precipitate.
The charge of the plastic tube could be causing the precipitate problem. Try the exact same order of additions, but in a glass tube.
Trial #65
   In glass tube: 0.3 ml Dentsply
      approx. 0.5 mg FD&C blue
      approx. 0.1 mg titanium dioxide→bright yellow
      25 ul Sucralose→turned green
      25 ul spearmint oil
      25 ul anethole
      25 ul vanilla creme #2961 (turned darker green)
   Mix, then add 0.5 ml pre-hydrated gel NO PRECIPITATE?

Conclusion

The plastic tube probably was causing the problems in samples #60 through 64 and not the order of additions. If the precipitate formed in glass tube #65, the particles remain so small that the mixture still looks homogeneous. In plastic tubes, the charge causes the ppt. particles to clump and form strands that stick to the test tube walls. Texture in gel #65 is still a little too loose. It's Kelcoloid HVF concentration is 0.99%. The texture of the last set of samples with good texture (#59) was 1.98%. Therefore 1.5% is probably sufficient.
   ***Try adding more phosphoric acid to sample #65 to see if
      1) the flavor is still o.k., just in case its 17.3% $H_3PO_4$ concentration is not enough for good etching
      2) the texture changes when added.
If another 200 ul of Dentsply (50% $H_3PO_4$) is added, 0.5 ml in total will have been added and bring final vol. up to 1.1 ml. Therefore, final dilution of Dentsply is 1.1/0.5=2.2X. So 50% is now down to 50%/2.2=22.72%.
Results
   Became less viscous liquid and taste is still o.k.
   A dentist stated that the best flavors are #56 and #57.
Object
   To add flavor formula to an existing etching gel formulation (Temrex "GelEtch") in glass tubes vs. plastic tubes.

Method
   Use preferred formulas #56 and #57 for flavoring GelEtch

| #56: formula | 0.3 ml Dentsply*<br>50 ul Sucralose<br>50 ul spearmint<br>25 ul vanilla #3043<br>0.8 ul hydrated Kelcoloid HVF* | #57: formula | 0.3 ml Dentsply<br>38 ul Sucralose<br>38 ul spearmint<br>25 ul van. creme<br>25 anise oil<br>0.6 ml Kelcoloid |
|---|---|---|---|

*For this expt (= Trial #66) use 1.1 ml GelEtch instead of these 2 ingredients
**Use 0.9 ml GelEtch instead of these 2 ingredients (= Trial #67)

To accurately measure the small volumes needed, calibrated a 127.5 mm long 100 $\mu l$ capillary tube in order to accurately deliver
   25 ul=15.937 mm
   50 ul=31.875 mm
   38 ul=24.22 mm
Added GelEtch into respective tubes first. Determined quantity by weight assuming that 1 gm=1000 ul. Then add flavors into tubes. Mix at end.

| Trial #66 (glass tube) | FINAL CONC. | | Trial #67 (plastic) |
|---|---|---|---|
| 1.1 ml GelEtch (35% $H_3PO_4$) | 31.4% | 30.7%<br>0.92 | 0.9 ml GelEtch<br>38 ul Sucralose |
| 50 ul Sucralose | 1.0 | 3.7 | 38 ul spearmint oil |
| 50 ul spearmint oil | 4.08 | 2.4 | 25 ul van. creme #2961 |
| 25 ul vanilla #3043 | 2.04 | 2.4 | 25 ul anise oil |
| 1.225 ml<br>Results: | Taste is excellent! | | 1.026 ml<br>Also excellent taste<br>Anise adds complexity<br>Try to further lower all ingredients |

| | | FINAL CONC. |
|---|---|---|
| Trial #68: | 0.9 ml GelEtch | 31.5% |
| | 30 ul Sucralose | 0.75% (21% less than in Trial #67) |
| | 30 ul spearmint oil | 3.0% (21% less than in Trial #67) |
| | 20 ul anise oil | 2.0% (20% less than in Trial #67) |
| | 20 ul vanilla creme #2961 | 2.0% (20% less than in Trial #67) |
| | 1.0 ml total vol. | |

Results
   Still tastes pretty good but acidity is more noticeable.

EXAMPLE 4

Prepare 2 part gel system that is reconstituted when needed. May have a 1 or 2 week shelf life if either gel or flavor is not stable for a longer period in a package. Part 1 may contain pre-hydrated gel, flavor, sweetener, color and part 2 would be the phosphoric acid.
Method
   Into 16 ml of water in a jar with a spinning magnetic stirring bar on a magnetic stirring plate, slowly add 39.6 mg Kelcoloid/ml=633.6 mg.

Add:
  0.05% FD&C Blue=8 mg (became too blue!)
  0.0625% titanium dioxide=10 mg
  0.0625% #03225 Turmeric yellow=10 mg Trial #69 OBJECT Make a good tasting formulation using Dentsply (50% $H_3PO_4$) and freshly made hydrated Kelcoloid HVF in glass tube.

|  |  | % final concentration |
|---|---|---|
| METHOD: | 0.6 ml hydrated Kelcoloid HVF = 23.7 mg | 2.12 |
|  | 35 ul Sucralose (25% solution) | 0.78 |
|  | 25 ul vanilla creme #2961 | 2.93 |
|  | 25 ul anise oil | 2.23 |
|  | 35 ul spearmint oil | 3.13 |
|  | 0.4 ml Dentsply (50% $H_3PO_4$) | 17.86 |
|  | 1.12 ml water | 71.65 |

Results

After final addition of $H_3PO_4$, color changed from blue to green and lost viscosity. Flavor is excellent!

Polyglycol—Dow Chemical Co. #7350 NF polyethylene glycol, which has a viscosity of 210 cp Silica—Degussa Sident 225 and Aerosil 200, which is preferred because of its smaller particle size. Generally, the smaller the particle size, the more preferred.

Trial #70
Method

Make gel without any flavor added. Add varying amounts of PADA (phenylacetaldehyde diisobutylacetone) to see if the horrible flavor of the phosphoric acid can be masked.

|  | % final concentration |
|---|---|
| 0.6 ml Hydrated Kelcoloid HVF = 23.76 mg | 2.376% |
| 0.4 ml Dentsply (50 % $H_3PO_4$) | 20% |
| 1.0 ml water | 77.62% |

Flavor of hydrated gel and Dentsply is not that bad!! It seems that Kelcoloid HVF itself has reduced the bad taste.

Trial #71

Add 12.5 ul PADA=1.23% PADA. Result: Muted the bitterness somewhat but added a flavor of its own that is objectionable.

Trial #72

Add 25 ul sucralose (25%)=0.6%. Result: Is now sweet and not too bad.

Trial #73

Add 25 ul Quest 7416969 Bubble Gum flavor. Result: Not too bad!!

***Try more sucralose and bubble gum flavor.

Trial #74

| Method: |  | % Final Conc. |
|---|---|---|
|  | 0.6 ml hydrated Kelcoloid HVF = 23.76 mg | 2.21 |
|  | 0.4 ml Dentsply (50% $H_3PO_4$) | 18.6 |

-continued

|  | % Final Conc. |
|---|---|
| 15 ul PADA | 1.395 |
| 30 ul sucralose (25%) | 0.7 |
| 30 ul bubble gum flavor | 2.79 |
| 1.075 ml |  |

Results

Taste is very good! Add more bubble gum and sucralose.

Trial #75

Add to trial #74 an additional 5 ul sucralose and 5 ul bubble gum flavor.

Results

Excellent! Final concentrations of ingredients:

|  | % Final Conc. |
|---|---|
| 0.6 ml hydrated Kelcoloid HVF = 23.76 mg | 2.19 |
| 0.4 ml Dentsply (50% $H_3PO_4$) | 18.4 |
| 15 ul PADA | 1.38 |
| 35 ul sucralose (25%) | 0.81 |
| 35 ul bubble gum flavor | 3.22 |
| 1.085 ml |  |

Trial #76
Object

Remake mixture from Trial #75, omitting PADA to compare its final taste. Determine least amount that must be added to make flavor acceptable.

|  |  | % Final Conc. |
|---|---|---|
| Method: | 0.6 ml hydrated Kelcoloid HVF = 23.76 mg | 2.22 |
|  | 0.4 ml Dentsply (50% $H_3PO_4$) | 18.69 |
|  | -no PADA- |  |
|  | 35 ul sucralose (25%) | 0.82 |
|  | 35 ul bubble gum flavor | 3.27 |
|  | 1.070 ml |  |

Results

This mixture is not quite as good as with PADA, but it isn't bad. It seems that alginate itself may diminish the harsh taste of phosphoric acid. Try adding sucralose and bubblegum to GelEtch (a silica/polyglycol gel).

Trial #77
Object

Add sucralose and bubble gum flavor to 1.0 ml GelEtch to see if PADA is necessary for this gel system.

|  | % Final Conc. |
|---|---|
| 1.0 gm GelEtch (35% $H_3PO_4$) | 32.7 |
| 35 ul sucralose (25%) | 0.82 |
| 35 ul bubble gum flavor | 3.27 |
| 1.07 ml |  |

Results

Taste is not too bad. Try adding 10 ul PADA into Trial #78: It tastes better with PADA flavor mask. Add more sucralose and more bubble gum flavor in next trial.

Trial #79

Object

Test with and without flavor mask (PADA) in polystyrene test tubes

| | % Final Conc. |
|---|---|
| 0.9 gm GelEtch (35% H$_3$PO$_4$) | 32.3 |
| 35 ul sucralose (25%) | 0.9 |
| 40 ul bubble gum flavor | 4.1 |
| 0.975 ml | |

Results

Excellent taste. Mixture may not need PADA!!

Trial #80

Remake formula #79 and add 5 ul PADA:

| | % Final Conc. |
|---|---|
| 0.9 gm GelEtch (35% H$_3$PO$_4$) | 32.1 |
| 35 ul sucralose (25%) | 0.89 |
| 40 ul bubble gum flavor | 4.08 |
| 5 ul PADA | 0.51 |
| 0.98 ml | |

Also excellent taste. Difficult to tell if PADA helped or not.

Trial #81

| | Trial #81 | Trial #82 | Trial #83 |
|---|---|---|---|
| Method: | | | |
| sucralose (25%) | 35 ul | 35 ul | — |
| Flavor Sci.-Natur., and artif. MX-731 Orange | 30 mg | — | — |
| Quest Orange-DY04424 | — | 30 mg | — |
| Dragoco Orange 9/798297 | — | — | 30 mg |
| Results: | Nice flavor | Also nice flavor | Not quite as good as previous 2 trials |

Sident 225 is an amorphous precipitated silicon dioxide hydrate thickener, whereas Aerosil 200 is an amorphous fumed silicon dioxide.

Trial #84

To make up a dental etch using Sident 225

| GelEtch Formula | Method: | |
|---|---|---|
| | Cost/100 gm of gel | Amt. needed/100 gm of gel |
| 42% water | — | 39 ml (fill up to 100 ml) |
| 13.3% ethanol | 11.7 c* | 13.3 ml @ ~ $4/lb. |
| .015% FD&C blue | — | 15 mg. |
| .02% #03225 turmeric yellow | — | 20 mg. |
| 5% polyglycol | 2.09 c | 5 gm @ $1.90/lb |
| 33% H$_3$PO$_4$ | 4.11 c* | 38.82 ml of 85% H$_3$PO$_4$ @ 56 c/lb for 100% material |
| 6.3% silica | 2.08 c | 6.3 gm Ashland Sident @ $1.50/lb |

*Try to minimize these 2 components to reduce cost and more easily make flavored product competitive.

Add 13.3 ml of ethanol to 39 ml water. Add colors. Add 5 gm polyglycol with constant stirring. Add 38.82 ml of 85% H$_3$PO$_4$. Finally, start adding 6.3 gm. Silica (Sident 225) powder very slowly.

Results

Color of solution is too dark. Next time, add 0.011% of each the blue and the yellow. Solution didn't thicken enough with the addition of 6.3% Sident silica. Continued to add 5 gms more. At 11.3 total grams, texture was not good. Added 4 gms more, 4 gms again, and finally 2 more gms. After a total of 21.3 gms, the texture was finally good!

| Actual Formula | % Final Solution |
|---|---|
| 38.82 ml of 85% H$_3$PO$_4$ | 28.14 |
| 39 ml water | 33.2 |
| 13.3 ethanol | 11.3 |
| 21.3 gm Sident silica | 18.1 |
| 5 gm Polyglycol | 4.25 |
| 0.015 gm FD&C blue | .012 |
| 0.02 gm #03225 Turmeric yellow | .017 |

Trial #85

Repeat Trial #84, but use Aerosil 200 silica (costs 2.66 times as much, but if one can use less than 8 grams (21.3/2.66), it's cost effective.

Methods

| Ingredient | Amount/100 gm of gel |
|---|---|
| 42% water | 39 ml |
| 13.3% ethanol | 13.3 ml |
| .011% FD&C blue | 11 mg |
| .011% #03225 turmeric yellow | 11 mg |
| 5% polyglycol | 5 gm |
| 33% H$_3$PO$_4$ | 38.82 ml of 85% H$_3$PO$_4$ |
| 6.3% silica | 6.3 gm Aerosil 200 silica |
| Totals: 99.62% | 100 gm |

Results

This gel is very thick (equivalent to Trial #84, which used 3.38 times as much silica). Aerosil 200 is the better silica to use and is also cost effective. Now try to reduce the alcohol.

Note: The ethanol probably insures the stability of the gel (prevents separation), and the polyethylene glycol prevents freezing when a product is shipped in varying weather conditions. Both are needed, but it may be possible to reduce them somewhat. Experimentation with freezing is the only way to test optimum concentrations.

Note: In the future, when ready to commercially prepare gel, consider using Aerosil 300, which has a smaller particle size, will yield a higher viscosity and will cost less. The problem is that it requires more energy to properly disperse.

Trial #86

Using Aerosil 200 silica gel stock formula containing sugar instead of Sucralose to keep cost down.

Method

| Ingredient | Amount |
|---|---|
| 29.7% water | 27 ml |
| 18.1% sugar | 20 g |
| 12.04% ethanol | 13.3 ml |
| .0081% FD&C blue | 9 mg |
| .0081% #03225 turmeric yellow | 9 mg |
| 4.53% polyglycol | 5 gm |
| 29.9% $H_3PO_4$ | 38.82 ml of 85% $H_3PO_4$ |
| 5.43% silica | 6.0 gm Aerosil 200 silica |
| Total: 99.72% | 110.483 gm |

Trial #87

Using stock gel from Trial #86, remove 1 ml of gel, and add previously used concentrations of flavors that worked well.

Method

Load sweetened gel into 3 ml syringe, and deliver 1 ml into polystyrene tube.
Add:
 3.13% spearmint oil=0.0313 ml=31.3 ul
 2.23% anise oil=22.3 ul
 2.23% vanilla creme #2961=22.3 ul
Mix gels and flavors. Taste with toothpick and rinse mouth with water flush containing bicarbonate of soda.

Results

Could use more sugar. Increase it by 50%. See if more flavors help too. Texture is perfect.

Trial #88

Increase each flavor by 50% to see effect.
Method
To 1 ml of gel in tube, add:
 1.5×3.13% spearmint oil=4.695%=46.95 ul
 1.5×2.23% anise oil=3.345%=33.45 ul
 1.5×2.23% vanilla creme #2961=3.345%=33.45 ul Results Doesn't Help. Still Needs to be Sweeter

Trial #89

Make a stock of sweetened gel using more sugar and fructose.

| Ingredient | Amount |
|---|---|
| 26.85% water | 27 ml |
| 24.75% sugar | 30 gm |
| 4.125% fructose | 5 gm |
| 9.9% ethanol | 12 gm |
| .0066% FD&C blue | 8 mg |

-continued

| Ingredient | Amount |
|---|---|
| 3.71% polyglycol | 4.5 gm |
| 25.94% $H_3PO_4$ | 37 ml of 85% $H_3PO_4$ |
| 4.7% Aerosil 200 | 5.7 gm |
| Totals: 99.98% | 121.208 gm |

To 1 ml of gel in tube, add:
 5.8% spearmint oil=64.3 ul
 2.23% anise oil=22.3 ul
 2.23% vanilla creme #2961=22.3 ul Results Still too sour. Add 22.3 ul more of each anise oil and vanilla creme. Pretty good taste. Try adding more of the vanilla next time to see if it cuts down on sourness.

Trial #90

Use proportionally more vanilla creme this time.
To 1 ml of gel in tube, add:
 3.13% spearmint oil=31.3 ul
 2.23% anise oil=22.3 ul
 4.46% vanilla creme #2961=44.6 ul
Better, but still needs more sweetness.

Trial #91

Add 0.4% Sucralose to the sweetened gel because it seems unlikely that enough Sucrose/Fructose can be added to achieve the needed sweetness to make 25% $H_3PO_4$ acceptable. Using Sucrose/Fructose has effectively reduced the exorbitant cost of Sucralose alone.

To 0.9 ml of gel, add 0.4 mg to reach 0.4%. If using 25% solution of Sucralose, must add 1.6 mg.
Add
 0.4% Sucralose=1.6 mg Sucralose
 3.13% spearmint oil=0.0313 ml=31.3 ul
 2.23% anise oil=22.3 ul
 2.23% vanilla creme #2961=22.3 ul
Better. Add another 1.6 mg Sucralose, which equals 0.8% Sucralose total. Tastes good.

Trial #92

To further minimize the use of Sucralose, due to its expense, re-make the stock of sweetened gel using only fructose and no Sucrose, with only half the usual amount of Sucralose.

| Ingredient | Amount |
|---|---|
| 25.09% water | 26 ml |
| 31.82% fructose | 40 gm |
| 0.39% Sucralose | 0.5 gm |
| 9.54% ethanol | 12 gm |
| .0064% FD&C blue | 8 mg |
| 3.57% polyglycol | 4.5 gm |
| 25.02% $H_3PO_4$ | 37 ml of 85% $H_3PO_4$ |
| 4.53% Aerosil 200 | 5.7 gm |
| Totals: 99.97% | 121.708 gm |

Without flavors added, the taste of the gel is not too bad.
To 1 ml of Sucralose sweetened gel (=1.322 gm) in tube, add:
 2.6% spearmint oil=35 ul
 2.0% anise oil=26 ul
 2.0% vanilla creme #2961=26 ul With flavors added, the taste is now very good, but could use slightly more flavor to be great.

Trial #93

Make 5 ml of fully flavored gel.

0.9 ml of gel weighs 1.19 gm. Therefore, 5 ml weighs 6.61 gm. Weigh this into a glass bottle, then add:

2.97% spearmint oil=21.2 ul
2.21% anise oil=15.8 ul
2.21% vanilla creme #2961=15.8 ul Final Formula

| Ingredient | Amount | |
|---|---|---|
| 23.24% water | 26 | ml |
| 29.47% fructose | 40 | gm |
| 0.368% Sucralose | 0.5 | gm |
| 8.84% ethanol | 12 | gm |
| .00589% FD&C blue | 8 | mg |
| 3.32% polyglycol | 4.5 | gm |
| 23.17% H$_3$PO$_4$ | 37 | ml of 85% H$_3$PO$_4$ |
| 5.0% Aerosil 200 | 5.7 | gm |
| 2.97% Spearmint oil | 4.03 | gm |
| 2.21% Anise oil | 3.0 | gm |
| 2.21% Vanilla creme | 3.0 | gm |
| Totals: 100.8% | 135.738 | gm |

Trial #94

To make orange flavored gel, take 1.9 ml of fully sweetened gel and add 25 ul of Mother Murphy's #002054 Orange Oil 5X.

Taste is very good.

Trial #95

To make cherry flavored gel, take 1.9 ml of fully sweetened gel and add 25 ul of Mother Murphy's #PH3043 Artificial Cherry Oil.

Also very good.

There has thus been shown and described a novel flavoring formulation for improving the taste of dental etching gels which fulfills all the objects and advantages sought therefor. Many changes, modifications, variations and other uses and applications of the subject invention will, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. A dental etch formulation comprising:
   acid which is effective to etch a surface of a tooth in an amount in the range of about 10 to about 40 percent by weight of the total formulation;
   sucralose in an amount in the range of about 0.37 percent to about 3 percent by weight of the total formulation; and
   fructose in an amount up to about 32 percent by weight of the total formulation.

2. The dental etch formulation of claim 1 wherein said acid includes phosphoric acid.

3. The dental etch formulation of claim 2 wherein phosphoric acid is present in an amount in the range of at least about 23 percent by weight of the total formulation.

4. The dental etch formulation of claim claim 2 wherein
   said phosphoric acid is present in an amount in the range of about 30 to about 40 percent by weight of the total formulation; and
   said sucralose is present in an amount from about 2 to about 3 percent by weight of the total formulation.

5. The dental etch formulation of claim 1 further comprising a flavoring agent.

6. The dental etch formulation of claim 5 wherein said acid includes phosphoric acid.

7. The dental etch formulation of claim 6 wherein said phosphoric acid is present in an amount in the range of at least about 23 percent by weight of the total formulation.

8. The dental etch formulation of claim claim 6 wherein
   said phosphoric acid is present in an amount in the range of about 30 to about 40 percent by weight of the total formulation; and
   said sucralose is present in an amount from about 2 to about 3 percent by weight of the total formulation.

9. The dental etch formulation of claim 5 wherein said flavoring agent is chosen from the group consisting of bubble gum flavor, grape flavor, cherry flavor, anise oil, cassia oil, vanilla, vanilla extract, vanilla creme, orange flavor, anethole, licorice, spearmint oil, phenylacetaldehyde diisobutyl acetal, strawberry flavor, and mixtures thereof.

10. The dental etch formulation of claim 9 wherein said acid includes phosphoric acid.

11. The dental etch formulation of claim 10 wherein said phosphoric acid is present in an amount in the range of at least about 23 percent by weight of the total formulation.

12. The dental etch formulation of claim 10 wherein
    said phosphoric acid is present in an amount in the range of about 30 percent to about 40 percent by weight of the total formulation; and
    said sucralose is present in an amount from about 2 to about 3 percent by weight of the total formulation.

13. A dental etch formulation comprising
    phosphoric acid in an amount in the range of about 23 to about 40 percent by weight of the total formulation;
    sucralose in an amount in the range of about 0.37 to about 0.39 percent by weight of the total formulation;
    fructose in an amount in the range of about 29 percent to about 32 percent by weight of the total formulation.

14. The dental etch formulation of claim 13 further comprising a flavoring agent.

15. The dental etch formulation of claim 14 wherein said flavoring agent is chosen from the group consisting of spearmint, anise, vanilla creme and combinations thereof.

16. The dental etch formulation of claim 15 wherein said flavoring agent is present in an amount in the range of 7 to 8 percent by weight of the total formulation.

17. The dental etch formulation of claim 14 wherein said flavoring agent is chosen from the group consisting of cherry and orange.

18. The dental etch formulation of claim 17 wherein said flavoring agent is present in an amount in the range of about 1 to 2 percent by volume of the total formulation.

19. A dental etch formulation comprising:
    acid which is effective to etch a surface of a tooth in an amount in the range of about 10 to about 40 percent by weight of the total formulation;
    xylitol in an amount in the range of about 20 percent to about 46 percent by weight of the total formulation;
    neohespiridin dehydrochalcone in an amount less than about 1 percent by weight of the total formulation;
    a first flavoring agent chosen from the group consisting of vanilla creme, vanilla extract, and combinations thereto; and
    a second flavoring agent chosen from the group consisting of licorice, anethole, and combinations thereto.

20. The dental etch of claim 19 wherein said acid includes phosphoric acid.

* * * * *